US006686316B2

(12) United States Patent
Zhang et al.

(10) Patent No.: US 6,686,316 B2

(45) Date of Patent: Feb. 3, 2004

(54) BIOCONTROL OF WEEDS

(75) Inventors: Wenming Zhang, Edmonton (CA); Michelle Sulz, Edmonton (CA)

(73) Assignee: Alberta Research Council Inc. (CA)

( * ) Notice: Subject to any disclaimer, the term of this patent is extended or adjusted under 35 U.S.C. 154(b) by 0 days.

(21) Appl. No.: 10/013,026

(22) Filed: Nov. 6, 2001

(65) Prior Publication Data

US 2002/0177528 A1 Nov. 28, 2002

(30) Foreign Application Priority Data

Nov. 6, 2000 (CA) ............................................ 2325215

(51) Int. Cl.[7] ............................ A01N 63/04; C12N 1/16

(52) U.S. Cl. ..................... 504/117; 504/150; 435/254.1

(58) Field of Search ................................ 504/117, 150; 435/254.1

(56) References Cited

PUBLICATIONS

Chung et al. "Potential of an Indigenous Fungus, *Plectosporium tabacinum*, as a Mycoherbicide for Control of Arrowhead (*Sagittaria trifolia*)". Plant Disease. 82:657–660. Jun. 1998.*

Smither–Kopperl et al. "*Plectosporium tabacinum*, a Pathogen of the Invasive Aquatic Weed Hydrilla verticillata in Florida". Plant Disease. 83(1):24–28. 1999.*

Hansen, Mary Ann. "Plectosporium Blight of Curcurbits". Virginia Cooperative Extension: Plant Disease Fact Sheets. Publication 450–709W. Virginia Tech. 2000.*

Hall, Linda.,et al. , "Resistance to acetolactate synthase inhibitors and quinclorac in biotype of false cleavers (*Galium spurium*)", *Wee Science, 46*, (Jul.–Aug. 1998), 390–396.

Makowski, Roberte., "Effect of Inoculum Concentration, Temperature, Dew Period, and Plant Growth Stage on Disease of Round–Leaved Mallow and Velvetleaf by *Colletotrichum gloeosporioides* f.sp. malvae", *Phytopathology, vol. 83, No. 11*, (1993), 1229–1234.

Malik, Najib.,et al. , "Growth and Development of False Cleavers (*Galium spurium* L.)", *Weed Science, vol. 35*, (1987),490–495.

Malik, N.,et al. , "The Biology of Canadian Weeds. 86. *Galium aparine* L. and *Galium spurium* L.", *Canadian Journal of Plant Science, 68*, (Apr. 1988),481–499.

Palm, Mary.,et al. , "*Plectosporium*, a new genus for *Fusarium tabacinum*, the anamorph of *Plectosphaerella cucumerina", Mycologia, 87*(*3*), (1993),397–406.

Tebeest, D.,et al. , "Temperature and Moisture Requirements for Development of Anthracnose on Northern Jointvetch", *Phytopathology, vol. 68*, (Mar. 1978),389–393.

Thomas, A.G. ,et al. ,"Weed Population Shifts in Alberta", *Agriculture and Agri–Food Canada, Saskatoon*, (1998), 1 page.

* cited by examiner

*Primary Examiner*—S. Mark Clardy
(74) *Attorney, Agent, or Firm*—Schwegman, Lundberg, Woessner & Kluth, P.A.

(57) ABSTRACT

The present invention is directed to a biocontrol agent *Plectosporium tabacinum* and methods for the biocontrol of weeds using the biocontrol agent. Preferably the weeds are cleavers (*Galium aparine* L and *Galium spurium* L.), and the biocontrol agent is *Plectosporium tabacinum* CL98–103 (ATCC deposit PTA-3463). The biocontrol agent is effective against herbicide-resistant and herbicide-susceptible cleavers, and it may be used in conjunction with other herbicides.

20 Claims, 8 Drawing Sheets

BIOCONTROL OF WEEDS

RELATED APPLICATION

The present invention claims priority from Canadian Application No. 2,324,215, filed Nov. 6, 2000, which application is incorporated herein by reference.

FIELD OF THE INVENTION

The present invention relates to the biocontrol of weed growth using a bioherbicide. More specifically, the present application pertains to the use of a fungal bioherbicide for the control of cleavers.

BACKGROUND OF THE INVENTION

Cleavers [false cleavers (*Galium spurium* L.) and cleavers (*G. aparine* L.)] are weeds of important economic impact in western Canada, especially for producers of canola (*Brassica napus* L. and *B. rapa* L.) (Malik and Vanden Born, 1988). Weed surveys in the prairie provinces of Canada have indicated that cleavers populations have increased during the past 10 years and their abundance ranking have increased more rapidly than other cropland weeds (Thomas, 1998). Heavy infestations of cleavers in canola cause severe yield losses, up to 18% with 100 false cleavers plants/$m^2$ through crop/weed competition (Malik and Vanden Born, 1987). Another problem with cleavers in canola is that cleavers seeds are similar in shape and size to canola seeds, making mechanical seed separation difficult. Cleavers seed contamination in canola leads to downgrading of canola quality, has implications for the crushing industry, and contributes to the spread of weed infestations. Under legislation in the Canada Seeds Act, no cleavers seed is allowed in pedigreed canola seed and thus pedigreed seed producers of canola cannot tolerate land infested with these weeds. Cleavers are not only difficult to control in canola but are an increasing problem in other major crops of Western Canada such as spring wheat (*Triticum aestivum* L.), barley (*Hordeum vulgare* L.), and pea (*Pisum sativum* L.).

Considerable efforts have been made to find effective herbicide controls for cleavers over the past decade. Chemical herbicides used for cleavers control include several acetolactate synthase (ALS) inhibitors along with auxin-type herbicide combinations. Unfortunately, herbicide resistance has been detected in populations of false cleavers (Hall et al., 1998). This herbicide-resistant false cleavers biotype shows cross-resistance to quinclorac and ALS inhibitors, including imazethapyr, one of the products for which herbicide-tolerant canola has been developed. With continuing herbicide use and herbicide-tolerant canola cultivation (approximately 20–40% or more of the canola acreage in Canada), herbicide resistance may become more common in false cleavers.

To date, no bioherbicides are available for control of cleavers. Thus, there is a need in the art for new or alternative cleavers control strategies. There is also a need in the art for cleaver control strategies for both conventional and herbicide tolerant (HT) canola. Further there is a need for biological control agents that complement herbicide use by introducing novel modes of action to mitigate herbicide resistance development and to provide a component within an integrated pest management system.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the biocontrol of weed growth using a fungal bioherbicide.

According to the present invention there is provided a biocontrol agent comprising *Plectosporium tabacinum* CL98–103. Preferably, the biocontrol agent comprises *Plectosporium tabacinum* CL98–103 deposit number PTA-3463 (ATCC).

Also according to the present invention, there is provided a composition comprising the biocontrol agent (*P. tabacinum* CL98–103) and a carrier. Any carrier that permits the biocontrol agent to be delivered to a target plant in a manner such that the biocontrol agent remains viable and pathogenic may be employed in the composition. Examples of carriers include, but are not limited to clay, alginate, diatomaceous earth, growth medium, or a combination thereof. The growth medium may comprise solid growth medium or liquid growth medium or a combination thereof. Solid growth medium may comprise potato dextrose agar, Czapek-Dox agar, lima bean agar, V-8 juice agar, oatmeal agar, tryptic soy agar, dextrose tryptone agar, Cooke rose bengal agar, prune agar, malt extract agar, synthetic nutrient poor agar, Sabouraud dextrose agar, water agar, cornmeal agar or a combination thereof. Liquid growth media may comprise V-8 juice medium, Modified Richard's solution (MRS), Yeast extract broth (YEB), Richard's solution (RS), Czapek-Dox broth (CDB), Trichoderma medium (TM), Tryptic soy broth (TSB), Potato dextrose broth (PDB), Nutrient broth (NB), Colletotrichum truncatum medium (CTM), Malt extract broth (MEB) or a combination thereof.

Also according to the present invention, there is provided a method for controlling weeds, herbicide-resistant and herbicide-susceptible cleavers, herbicide-resistant and herbicide-susceptible false cleavers, and other weeds by infecting them with the biocontrol agent defined above. The biocontrol agent may be administered to the cleavers in combination with a herbicide. Preferably, the biocontrol agent is administered to the weeds at about the one whorl stage or earlier.

Further according to the present invention as defined above, the biocontrol agent or composition comprising the biocontrol agent may additionally comprise a surfactant. Preferably the surfactant is Silwet L-77, and is present in an amount of about 0.05% to about 0.1% by volume.

Also according to the present invention as defined above, there is provided a composition comprising spores of *Plectosporium tabacinum* CL98–103 and a carrier.

Further, according to the present invention there is provided a method for the biocontrol of a weed plant under non-aquatic conditions, or conditions that do not requiring periodic submersion, using *Plectosporium tabacinum* as a biocontrol agent.

Also according to the present invention, there is provided a method for growing and producing spores of *Plectosporium tabacinum* CL98–103, comprising growing the fungal biocontrol agent or spores thereof in a suitable liquid medium.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1A shows spread plate cultures of biocontrol agent CL98–103 grown on PDA with continuous light. FIG. 1B shows single spore cultures of biocontrol agent CL98–103 grown on PDA with continuous light. FIG. 1C shows conidiophores of biocontrol agent CL98–103. FIG. 1D shows a condium of biocontrol agent CL98–103. FIG. 1E shows two conidia of biocontrol agent CL98–103. FIGS. 1F–H show germinated conidia of biocontrol agent CL98–103.

FIG. 2 shows the disease reaction of false cleavers caused by fungal biocontrol agent CL98–103.

FIG. 7A) and in submerged liquid culture using Richard's solution (filled squares), modified Richard's solution (filled circles), potato dextrose broth (filled triangles), and yeast extract broth (filled diamonds; FIG. 7B). On standard agar media, the number of spores per plate was determined after 21 d incubation. For submerged liquid culture, the number of spores per ml was determined after 3 d incubation. Results of two trials with three replicates per trial were combined for each medium. Standard errors are indicated by vertical bars.

DESCRIPTION OF PREFERRED EMBODIMENT

Figure 1:
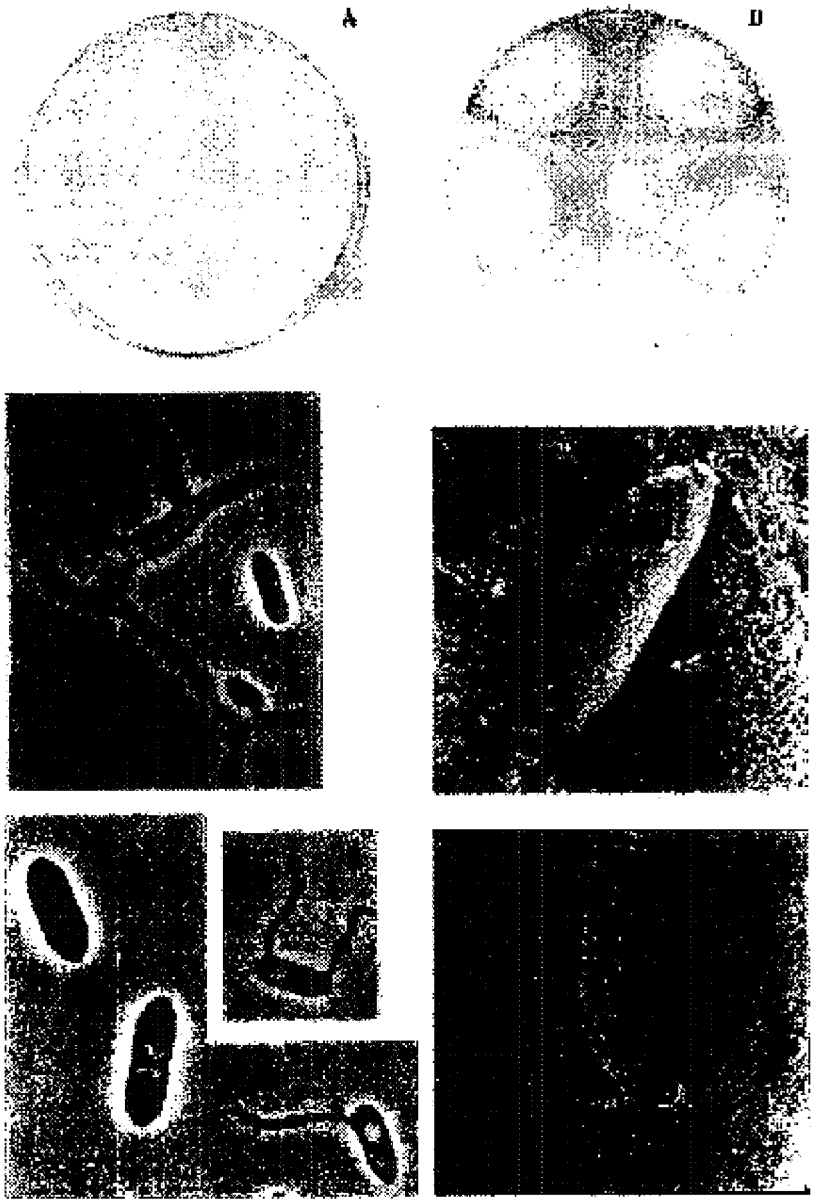
FIG. 1 shows characteristics of biocontrol agent CL98–103.

The present invention relates to the biocontrol of weed growth using a fungal bioherbicide.

The following description is of a preferred embodiment by way of example only and without limitation to the combination of features necessary for carrying the invention into effect.

The present invention provides a fungal bioherbicide of the Plectosporium species. The present invention also provides a method to control both herbicide-resistant and herbicide-susceptible cleavers (*Galium aparine* L. and *G. spurium* L.). The method comprises applying an effective amount of *P. tabacinum* to the weeds.

By "biocontrol agent" or "bioherbicide" it is meant an organism, typically a plant pathogen, that reduces the growth rate, development, or both the growth rate and development (as evidenced by reduced dry weight), possibly leading to death, of at least one target plant species. Preferably, the biocontrol agent exhibits selective activity (host specificity) when exposed to one or more plants, so that a plant of interest is not affected by the biocontrol agent, while one or more target plants, for example a weed species, is susceptible to the effects of the biocontrol agent. The present invention provides a fungal bioherbicide of the Plectosporium species. Preferably the fungus is a *P. tabacinum* (van Beyma) strain CL98–103. More preferably, the fungus is *P. tabacinum* deposited at the ATCC (10801 University Blvd., Manassas, Va. 20110–2209) as PTA-3463, on Jun. 19, 2001.

By "plant of interest" it is meant the plant species for which growth is desired when exposed to a biocontrol agent. Plants of interest may include horticultural and agriculturally important species. Without wishing to be limiting, a plant of interest may be selected from the group consisting of canola (*Brassica napus* and *B. rapa*), spring wheat (*Triticum aestivum* L.), barley (*Hordeum vulgare* L.), pea (*Pisum sativum* L.), cauliflower (*Brassica oleracea* L.), oats (*Avena sativa* L.), alfalfa (*Medicago sativa* L.), lentil (*Lens culinaris* Medic.), flax (*Linum usitatissimum* L.), sunflower (*Helianthus annuus* L.), safflower (*Carthamus tinctorius* L.), potato (*Solanum tuberosum* L.), tomato (*Lycopersicon esculentum* L.), tobacco (*Nicotiana tabacum* L.), balsam (*Impatiens balsami* L.), celery (*Apium graveolens* L), parsnip (*Pastinaca sativa*), violets (*Viola odorata*), melon (*Cucumis melo* L.), zucchini (*Cucurbita pepo* L.), and pumpkin (*Cucurbita pepo* L). However, it is to be understood that other plants may also be considered a plant of interest providing that they are not susceptible to the effects of *P. tabacinum.*

By "target plant" it is meant one or more plants that are susceptible to the effects of the biocontrol agent and exhibit reduced growth, development or death when exposed to the biocontrol agent. Target plants are typically weed species, for example but not limited to herbicide-resistant and herbicide susceptible cleavers (*Galium aparine* L. and *Galium spurium* L.).

*Plectosporium tabacinum* has been suggested as a potential bioherbicide against arrowhead (*Sagittaria trifolia* L.), a weed difficult to control in rice fields in Korea (Chung et al., 1998), and hydrilla (*Hydrilla verticillata* (L.F.) Royle), an invasive aquatic weed in the Southeastern United States (Smither-Kopperl, 1999). Differences in the growth characteristics and host specificity between the *P. tabacinum* strain of the present invention and these other isolates suggest that the *P. tabacinum* fungal strain of the present invention is different from the other isolates. However, the biocontrol agent of the present invention has not been suggested for use in non-aquatic environments, or with plants that are not exposed to periodic submersion. Therefore, in an aspect of an embodiment of the present invention, which is not meant to be considered limiting in any manner, there is provided the use of *P. tabacinum*, preferably *P. tabacinum* (van Beyma) strain CL98–103, or more preferably, *P. tabacinum* deposited at the ATCC as PTA-3463 for the control of weeds under more arid conditions, that do not involve continuous, or prolonged water exposure regimes.

Referring now to FIG. 1, the fungal biocontrol agent as described herein, grown on potato dextrose agar exhibits colonies that are moist, translucent white to pink in colour, radially furrowed with concentric rings and with a felty appearance. Further characteristics of fungal biocontrol agent are described in Example 1.

Figure 2A:
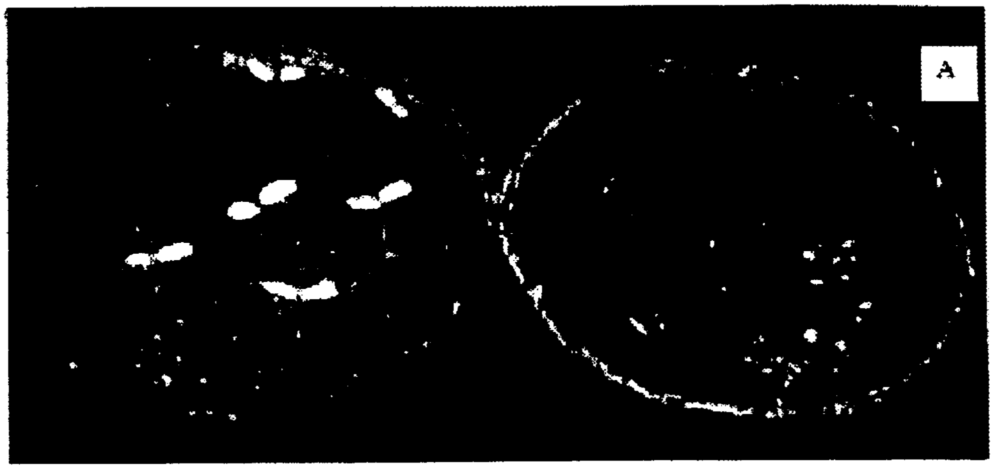
FIG. 2A shows false cleavers at the cotyledon stage that have been treated with fungal biocontrol agent (right) or untreated (left).
Figure 2B:
FIG. 2B shows false cleavers at the 1-whorl stage that have been treated with fungal biocontrol agent (right) or untreated (left).

Seedlings at the cotyledon or 1-whorl stages are at the most suitable stage for chemical application (Malik and Vanden Born, 1988, Phytopathol. 83:1229–1234). Referring now to FIG. 2, there is shown the effect of *P. tabacinum*, in this case strain CL98–103, on false cleavers seedlings at the cotyledon stage (FIG. 2A) and one whorl stage (FIG. 2B). The plants shown on the left are treated with a composition that lacks *P. tabacinum* CL98–103 whereas plants on the right are treated with *P. tabacinum* CL98–103. The results indicate that fungal biocontrol agent *P. tabacinum* may be employed for the control of false cleavers. Further, as indicated in Table 1 of Example 2, *P. tabacinum* caused large necrotic lesions on leaves and stems of herbicide-resistant and herbicide-susceptible false cleavers seedlings but was not pathogenic to herbicide-resistant or herbicide susceptible canola suggesting that the fungal strain of the present invention may be employed to control false cleavers in canola.

Figure 3A:
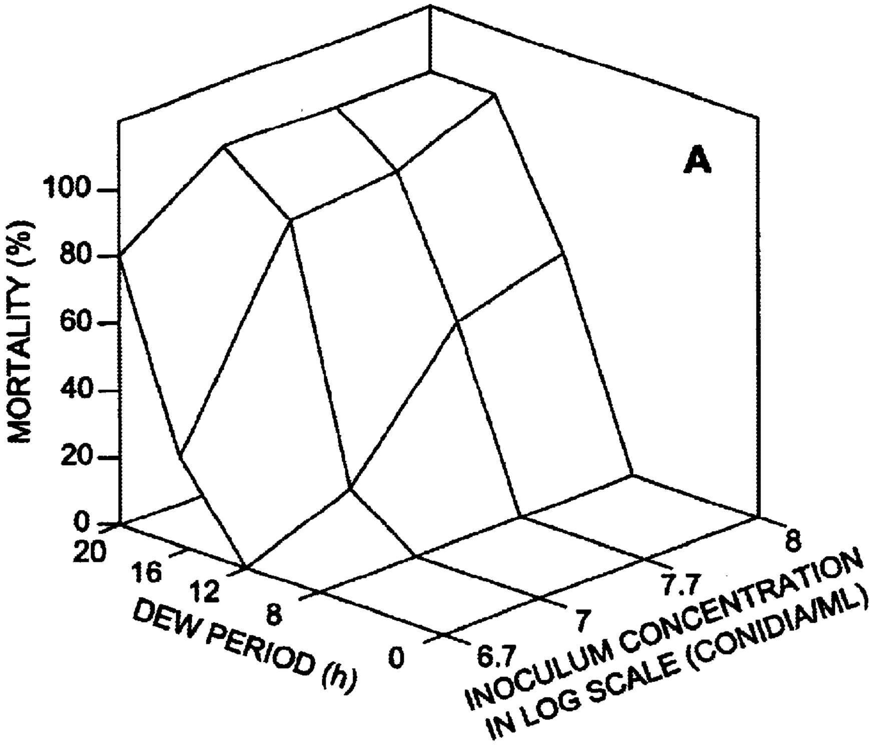
FIG. 3 shows the effect of inoculum concentration and dew period duration on disease development caused by *Plectosporium tabacinum* CL98–103 on false cleavers, expressed as percent mortality (FIG. 3A) and reduction in dry weight (FIG. 3B) seven days after inoculation. False cleavers seedlings at the 1-whorl stage were inoculated with conidial suspension at a concentration of $5\times10^6$, $1\times10^7$, $5\times10^7$, or $1\times10^8$ conidia/ml in 1% gelatin solution. Dew temperature was 22° C. (in dark) and plants were placed in the dew chamber for 9, 12, 16, or 20 h and then returned to the greenhouse. Data represent the mean of three replicates.
Figure 3B:
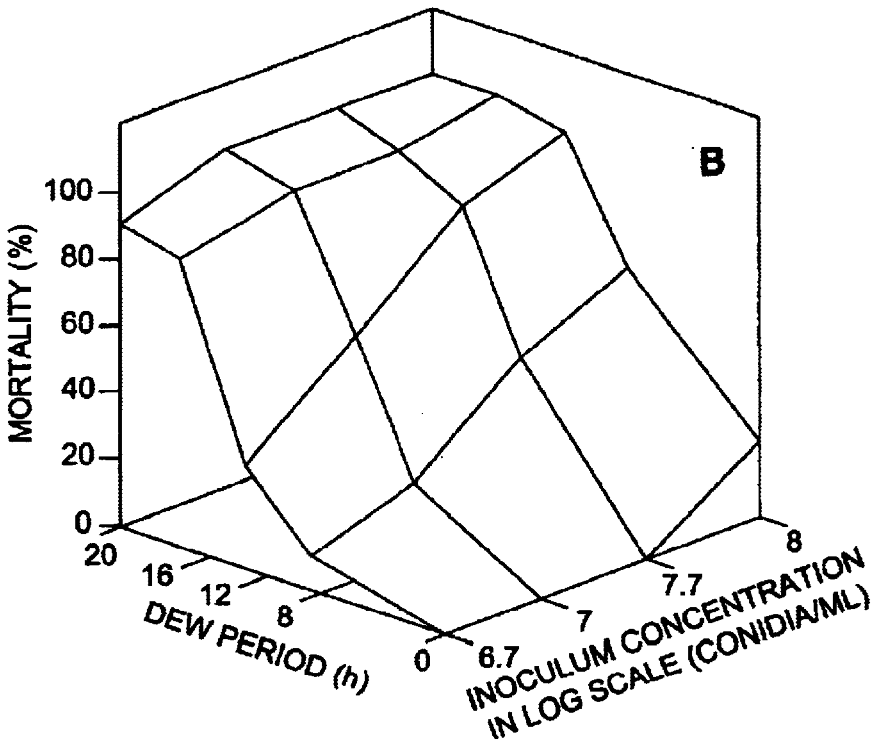

Referring now to FIG. 3, the biocontrol agent of the present invention kills false cleavers seedlings when applied to seedlings at a concentration of about $10^7$ spores per mL and with a dew period of about 16 to 24 hours (FIG. 3A). However, other application doses in combination with other dew periods were capable of reducing the dry weight of false cleavers plants (FIG. 3B) suggesting that *P. tabacinum* may permit a plant of interest, for example, but not limited to canola to out compete false cleavers weeds in a field. Collectively, these results suggest that *P. tabacinum* may be employed as a biocontrol agent for false cleavers weeds.

Figure 4A:
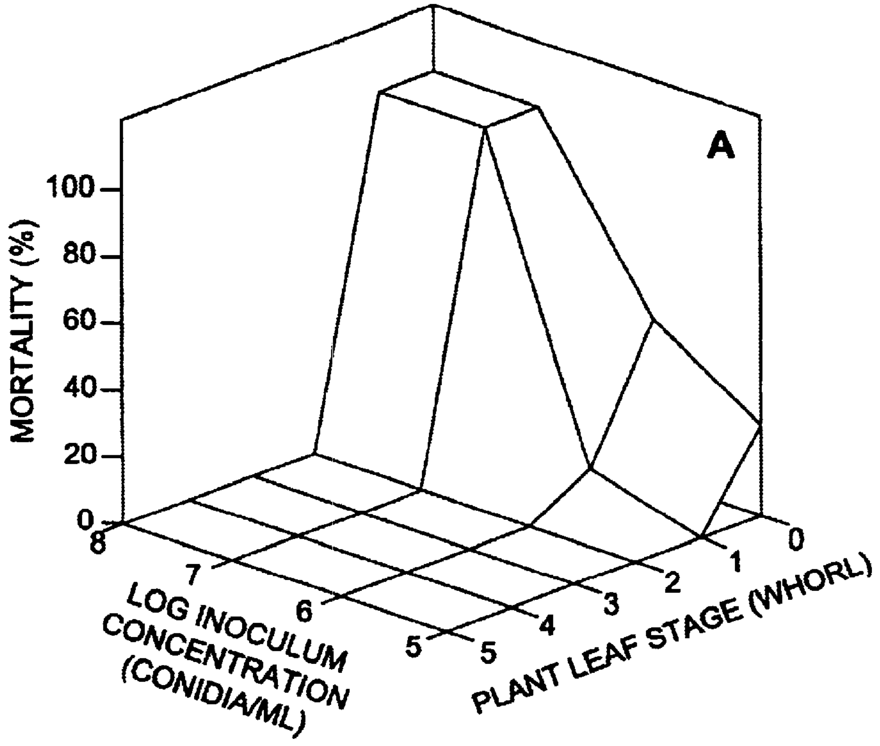
FIG. 4 shows the effect of *Plectosporium tabacinum* CL98–103 inoculum concentration and plant growth stage on the control of false cleavers, expressed as percent mortality (FIG. 4A) and reduction in dry weight (FIG. 4B) seven days after inoculation. Seedlings of false cleavers at the cotyledon, and 1-, 2-, 3-, 4- or 5-whorl growth stage were inoculated with a conidial suspension at concentrations of $1\times10^8$, $1\times10^7$, $1\times10^6$, $1\times10^5$ or 0 spores/ml in 1% gelatin solution. After inoculation, pots with inoculated seedlings were placed in a dark dew chamber for 24 h. Data represent the mean of three replicates.
Figure 4B:
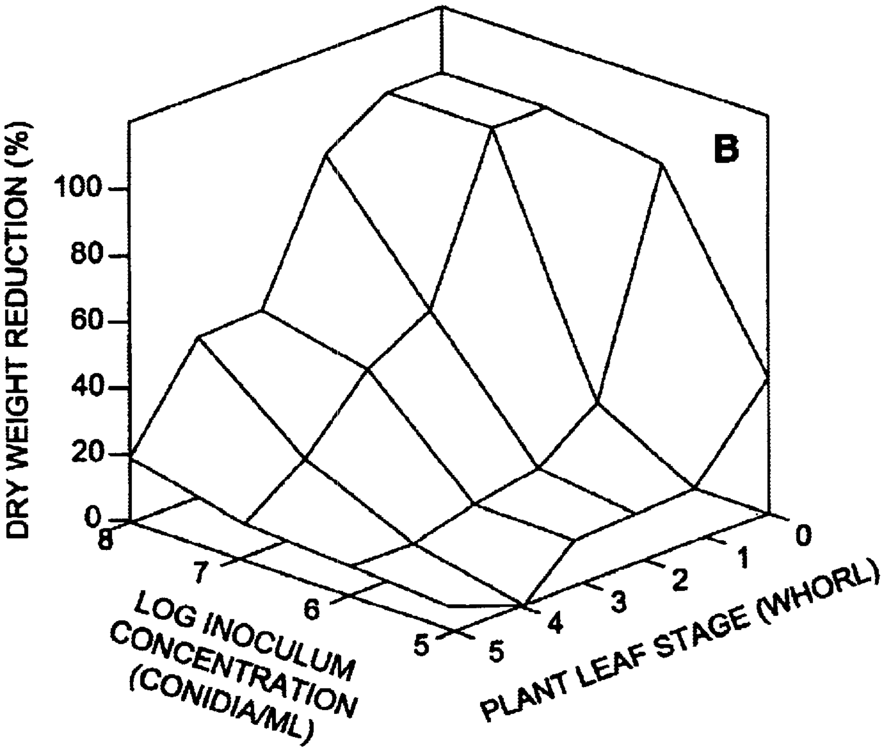

Referring now to FIG. 4, there is shown the effect of inoculum concentration of *P. tabacinum*, for example *P. tabacinum* CL98–103, and cleaver leaf stage on the mortality and percent dry weight reduction of false cleavers plants. As suggested by the results of FIG. 4A one hundred percent mortality of false cleavers is observed with an inoculum concentration of $10^7$ conidia per mL and the cleavers growth stage is between about the cotyledon stage and the 1-whorl stage. However, other inoculum doses also caused significant mortality of false cleavers plants. Further, as shown by the results depicted in FIG. 4B, various inoculum concentrations when applied to false cleavers at growth stages between about the cotyledon and 5 leaf stage exhibited a dry weight reduction of false cleavers suggesting that *P. tabacinum* CL98–103 may permit a plant of interest to outcompete false cleavers weeds in a field. Preferably, the biocontrol agent of the present invention is applied to false cleavers when the weeds are at a growth stage of about the 1-whorl stage or earlier. Further, it is preferable that the biocontrol agent of the present invention be applied at a concentration of about $1\times10^7$ conidia per mL or greater. However, increasing the inoculum concentration may be used in the biocontrol of older false cleavers seedlings and such an application is fully contemplated by the present invention.

Therefore, the present invention provides a method for the biocontrol of one or more weeds, for example, but not limited to false cleavers, using the fungus *P. tabacinum*. Preferably the fungus is a *P. tabacinum* (van Beyma) strain CL98–103. More preferably, the fungus is *P. tabacinum* deposited at the ATCC as PTA-3463. Furthermore, the use of the biocontrol agent as described herein may be supplemented with one or more chemical herbicides as required.

Efficacy and host specificity are the two major criteria in the selection of suitable plant pathogens as weed biocontrol agents. As described in more detail in the examples, the fungus *P. tabacinum* caused mortality in false cleavers and cleavers seedlings. Therefore, *P. tabacinum* acts as a biocontrol agent and has the potential to control cleavers. Moreover, *P. tabacinum* also exhibited similar effects on herbicide-resistant, and herbicide-susceptible cleavers (*Galium aparine* L. and *G. spurium* L).

*P. tabacinum* was non-pathogenic to canola, regardless of species and novel traits (herbicide tolerant vs conventional cultivars). Thus, *P. tabacinum* can be safely used in canola for false cleavers control. Further, *P. tabacinum* is non-pathogenic towards other commercially important plants, for example, but not limited to, wheat (*Triticum aestivum* L.), barley (*Hordeum vulgare* L.), oats (*Avena sativa* L.), alfalfa (*Medicago sativa* L.), pea (*Pisum sativum* L.) and lentil (*Lens culinaris* Medic.). A minor response was observed in response to application of *P. tabacinum* to flax, safflower, melon, zucchini, and tomato when these plants were subjected to a 24 h dew period treatment. However, the lesions covered less than about 3% of the infected leaves and did not expand during a two-week-long observation period. In total, host specificity tests on 35 plant species in 26 genera and 12 families demonstrated that *P. tabacinum* is safe to use and that *P. tabacinum* is an effective biocontrol agent for cleavers (see Table 4, Example 2).

Figure 5:
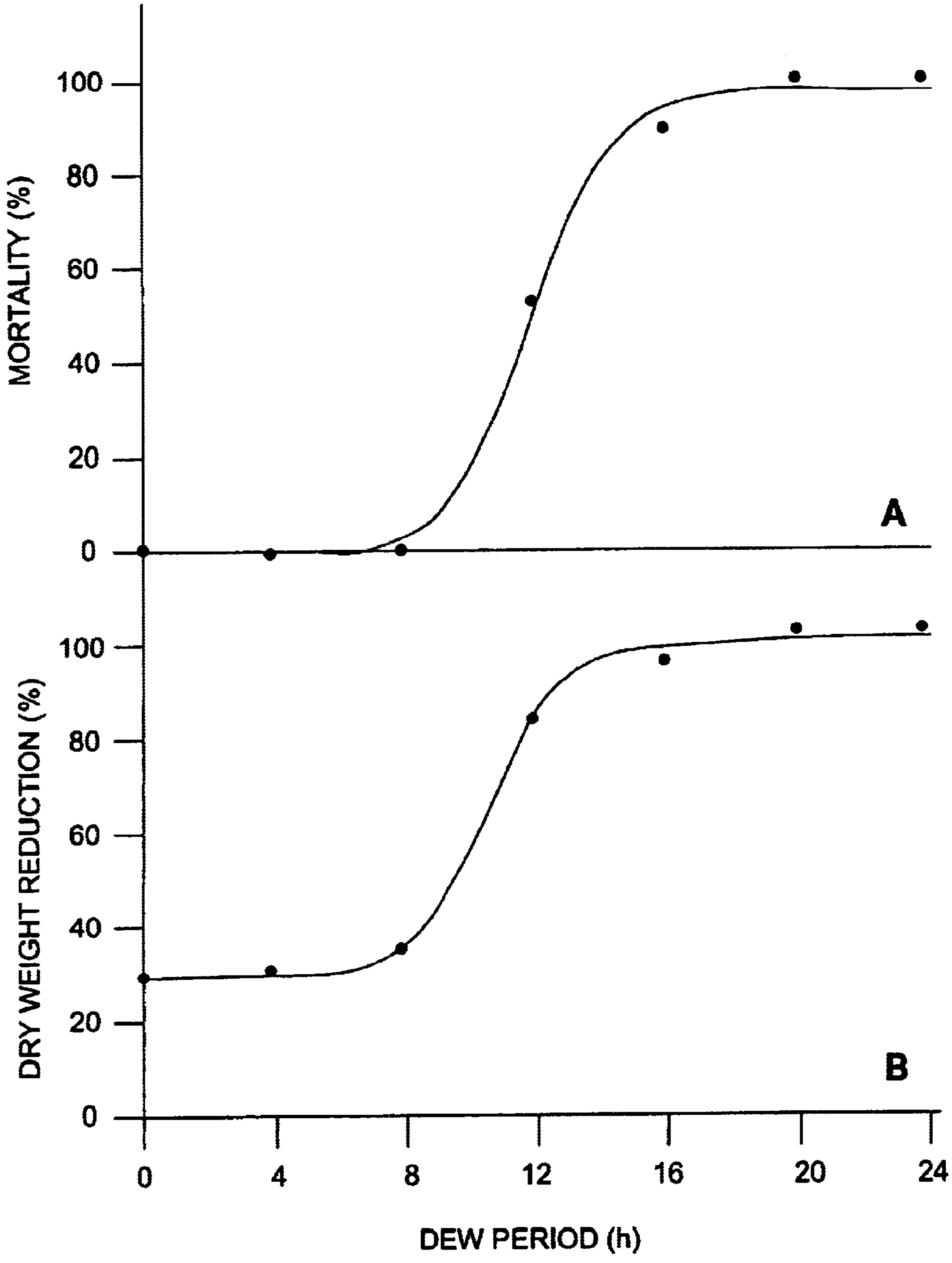
FIG. 5 shows the effect of dew period on disease development caused by *Plectosporium tabacinum* CL98–103 on false cleavers, expressed as percent mortality (FIG. 5A) and reduction in dry weight (FIG. 5B) seven days after inoculation. Seedlings of false cleavers at the 1-whorl growth stage were inoculated with a conidial suspension at a concentration of $1\times10^7$ conidia/ml in 1% gelatin solution. Dew temperature was 22° C. (in dark). Data represent the mean of three replicates.

Pathogen inoculum concentration, plant growth stage, dew period and temperature have been recognized as important pathogen, plant, and environment components that contribute to the efficacy of a bioherbicide (TeBeest, 1991, Ecology and epidemiology of fungal plant pathogens studied as biological control agents of weeds. pp. 97–114 in TeBeest, D.O. (ed) Microbial Control of Weeds. Chapman & Hall, New York; Yang and TeBeest, 1993, Phytopathol. 83:891–893). Referring now to FIG. 5, there is shown the effect of dew period duration on the mortality and dry weight reduction of false cleavers after spraying the weeds with about $1\times10^7$ spores per mL of *P. tabacinum*, in this example strain CL98–103. One hundred percent mortality of false cleavers seedlings was observed with a dew period duration of about 16 hours or longer, but shorter dew periods also promoted significant mortality of false cleavers (FIG. 5A). Further, dew periods of about 12 hours or longer promoted a dry weight reduction of false cleavers in the range of about 80% or greater, while dew periods less than about 12 hours also resulted in substantial dry weight reduction of false cleavers.

The minimum dew period to achieve about 100% mortality of false cleavers seedlings is dependent on temperature (Table 2, Example 2). At a dew period temperature of about 22° C., the minimum dew period to achieve about 100% mortality of false cleavers was about 16 h (FIG. 5). This dew period requirement is similar to those reported for other bioherbicides including *Colletotrichum gloeosporioides* f.sp. malvae (TeBeest et al., 1978, Phytopathol. 68:389–393; Makowski, 1993, Phytopathol. 83: 1229–1234). Dew period requirements of 16 h or longer may limit the practical use of fungi as biological control agents for weeds. However, the addition of a surfactant, for example, but not limited to Silwet L-77 in combination with the biocontrol agent of the present invention reduces the dew period for mortality of cleavers. For example, but not wishing to be limiting, the addition of about 0.05% to about 0.1% Silwet L-77 decreased the minimum dew period for 100% mortality of *G. spurium* to 12 h. Eight-hour dew also caused more than about 70% mortality and greater than about 80% dry weight reduction.

Repetitive dew periods are known to shorten the optimal dew period required for mortality of weeds such as *Senna obtusifolia* by *Alternaria cassiae* and Echinochloa species by *Exserohilum monoceras*. Similar results are obtained with the biocontrol agent of the present invention. As described herein (Table 3, Example 2), multiple, repetitive dew periods, that more closely simulate field conditions than a single long dew period, exhibited enhanced control of false cleavers seedlings.

Therefore, *P. tabacinum* may introduce one or more novel modes of action to mitigate herbicide resistance development in cleavers and can be considered as a component for herbicide resistant cleavers management.

Figure 6:
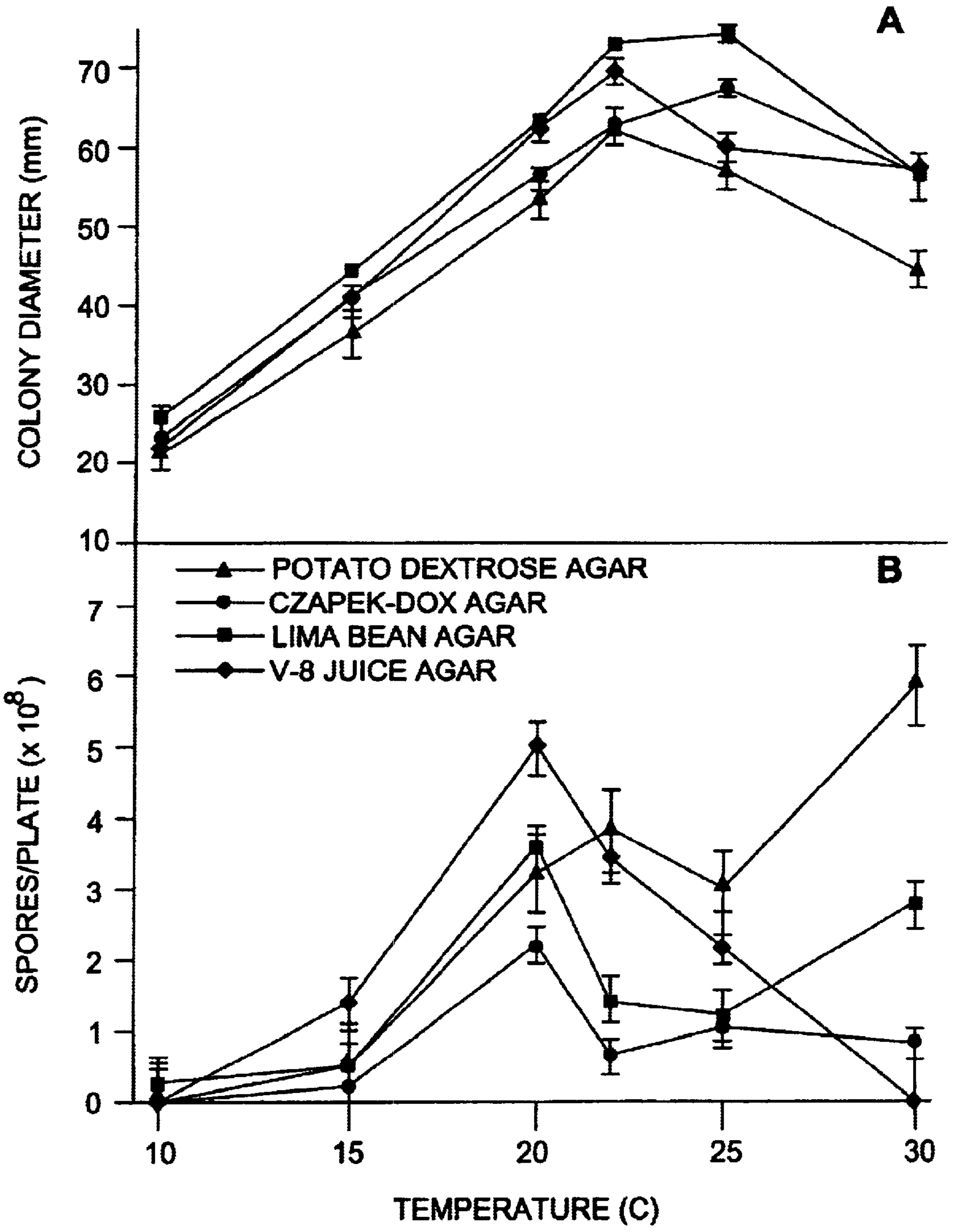
FIG. 6 shows the effect of temperature on radial mycelial growth (FIG. 6A) and spore production (FIG. 6B) of *Plectosporium tabacinum* CL98–103 on potato dextrose agar (PDA), Czapek Dox agar (CDA), lima bean agar (LBA) and V-8 juice agar (VA). The number of conidia per plate was determined after 21 d incubation while mycelial growth was measured after 14 d incubation. Results of two trials with three replicates per trial were combined for each medium. Standard errors are indicated by vertical bars.

Radial mycelial growth, conidium production, and conidial germination of *P. tabacinum*, for example but not limited to *P. tabacinum* CL98–103, responded differently to changes in nutritional and environmental conditions. Referring now to FIG. 6, there is shown the effect of temperature on the growth and spore production of *P. tabacinum* CL98–103 on different agar media. The results suggest that a variety of agar media, for example but not limited to potato dextrose agar, Czapek-Dox agar, lima bean agar, and V-8 juice agar may be employed for the growth and spore production of *P. tabacinum* CL98–103. Other agar types which may be used for growth and spore production of *P. tabacinum* CL98–103 include, but are not limited to oatmeal agar, tryptic soy agar, dextrose tlyptone agar, Cooke rose bengal agar, prune agar, malt extract agar, synthetic nutrient poor agar, Sabouraud dextrose agar, water agar and cornmeal agar (Table 5, example 3). A preferred temperature range for mycelial growth was between about 20° C. and about 30° C., but temperatures outside this range are also acceptable for growth of *P. tabacinum* CL98–103 (FIG. 6). An effective temperature for sporulation was about 20° C. or about 30° C. depending on upon the nutrient medium. For example, but not wishing to be limiting, sporulation of *P. tabacinum* CL98–103 on, Czapek-Dox agar, lima bean agar, and V-8 juice agar was high at a temperature of about 20° C., while sporulation on potato dextrose agar was high at a temperature of about 30° C.

Figure 7:
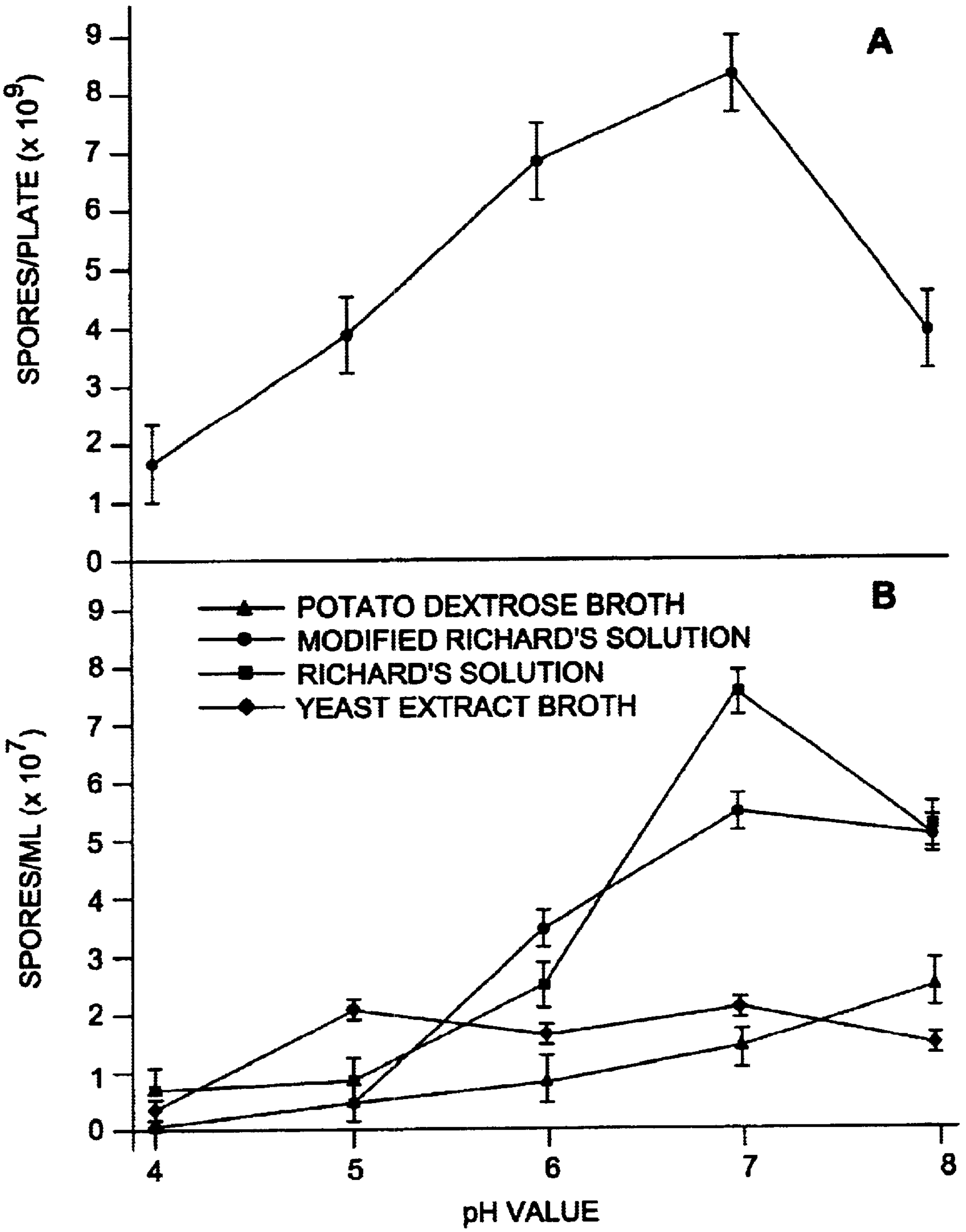
FIG. 7 shows the effect of pH on spore production of *Plectosporium tabacinum* CL98–103 on standard agar media (potato dextrose agar.

Referring now to FIG. 7, there is shown the effect of medium pH on spore production of *P. tabacinum*, for example but not limited to *P. tabacinum* CL98–103, grown on potato dextrose agar (FIG. 7A) and in different liquid culture media (FIG. 7B). The results indicate that a variety of liquid culture media may be employed for the growth and spore production of *P. tabacinum*, and that media of different pHs may be employed for growth and spore production. As shown in FIG. 7B, spore production observed for media with a pH in the range of about 6 to about 8, was generally higher than spore production observed for the same media at lower pH values. The present invention contemplates growing *P. tabacinum* on any suitable solid medium or in any suitable liquid culture medium. Further, the present invention contemplates spore production of *P. tabacinum* on any suitable solid medium or in any suitable liquid culture medium. Also, the present invention contemplates formulations of *P. tabacinum*, spores of *P. tabacinum*, or a combination thereof on any suitable solid medium or in any suitable liquid culture medium. Preferably the *P. tabacinum* is strain CL98–103 (van Beyma).

Figure 8:
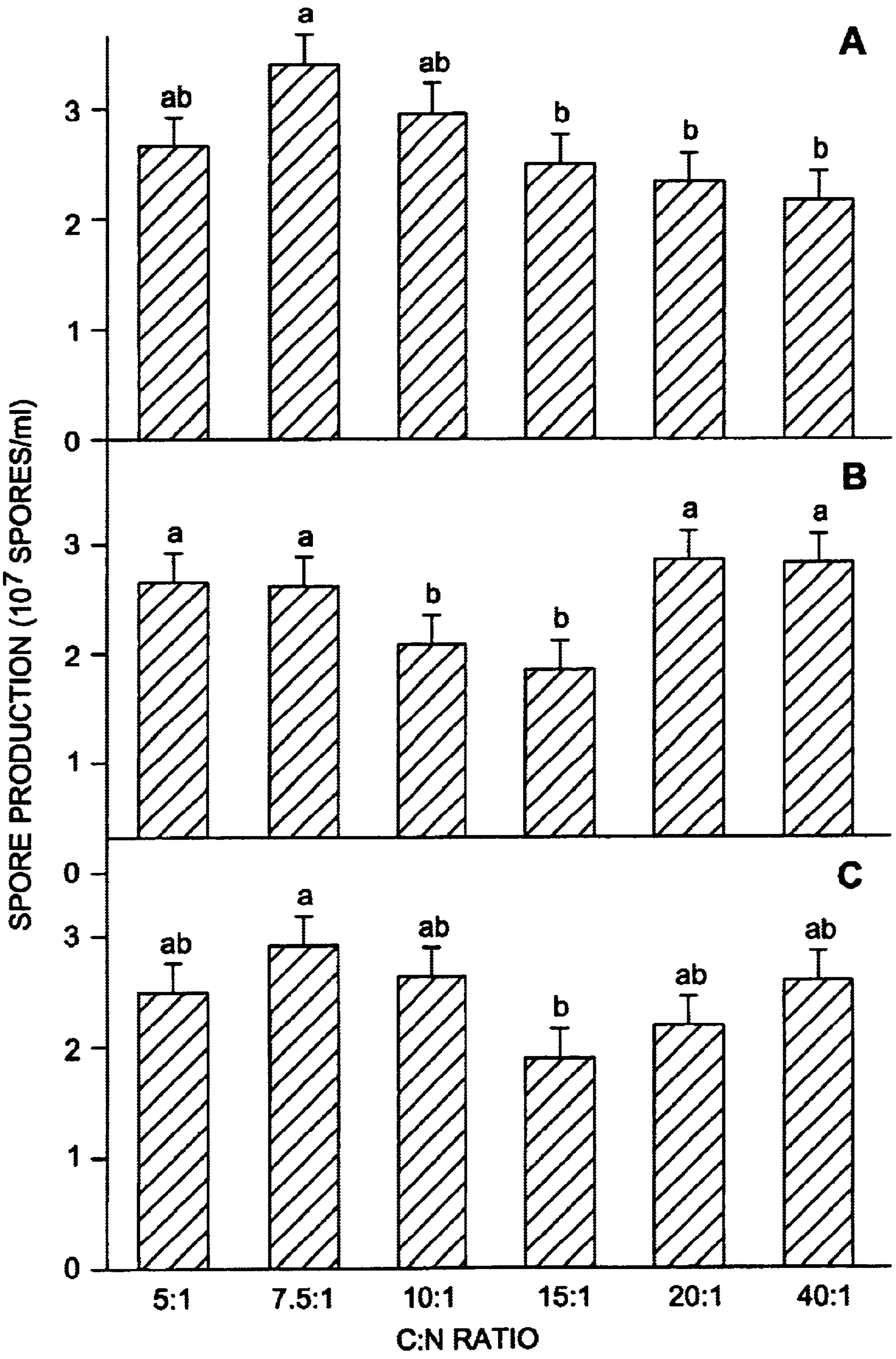
FIG. 8 shows the effect of carbon-to-nitrogen ratio on spore production of *Plectosporium tabacinum* CL98–103 in a basal salt medium of Richard's solution. Media with three carbon (sucrose) and nitrogen ($KNO_3$) concentrations and six different ratios of carbon to nitrogen (C:N) was prepared. Media with sucrose concentrations of 8.4 (FIG. 8A), 21 (FIG. 8B), and 33.6 (FIG. 8C) g $L^{-1}$ and C:N rations of 40:1, 20:1, 15:1, 10:1, 7.5:1, and 5:1 were prepared. Spore production in unmodified Richard's solution (50 g $L^{-1}$ sucrose and a 15:1 C:N ratio) was included as a control. The number of spores per ml was determined after 3 days incubation on an orbit shaker at 150 rpm.

Referring now to FIG. 8, there is shown the effect of the carbon:nitrogen (C:N) ratio of the medium on spore production of *P. tabacinum* for medium comprising 8.4 (FIG. 8A), 21 (FIG. 8B) and 33.6 g $L^{-1}$ sucrose (FIG. 8C). The results shown in FIG. 8 indicate that different media, comprising a range of sugars, for example, but not limited to sucrose and exhibiting a range of C:N ratios may be employed for the growth and spore production of *P. tabacinum*. Without wishing to be limiting nitrogen sources may include, but are not limited to potassium nitrate, corn gluten meal, corn steep liquor, glutnmic acid, asparagines, casamino acids, yeast extract, sodium nitrate, casein, urea, malt extract, ammonium sulfate, bovine serum albumin, cottonseed oil, or a combination thereof. Carbon sources may comprise, but are not limited to sucrose, galactose, corn starch, cellulose, glucose, fructose, citric acid or a combination thereof.

As described in Example 3, *P. tabacinum* produces large quantities of spores in liquid fermentation medium within 3 d when the initial spore concentration is about $5\times10^4$ spore/ml. Thus, spore production is not a limiting factor for the development of this fungus as a bioherbicide for control of cleavers.

Thus, in an aspect of an embodiment of the present invention, there is provided a method of controlling cleavers (*Galium aparine* L. and *G. spurium* L) that comprises applying an effective amount of biocontrol agent *P. tabacinum* to the cleavers. Preferably the *P. tabacinum* is (van Beyma) strain CL98–103. The cleavers may comprise herbicide-resistant cleavers, herbicide-susceptible cleavers or a combination thereof. Further, the present invention contemplates preventative control of cleavers, for example, but not limited to, applying an effective amount of biocontrol agent *P. tabacinum*, preferably *P. tabacinum* (van Beyma) strain CL98–103, to prevent emergence of cleavers. Preferably, the effective amount of *P. tabacinum* strain CL98–103 is in the range of about $1\times10^5$ to about $1\times10^8$ spores per mL and the cleavers are sprayed until runoff. However, spore concentrations outside this range may be employed if desired.

The biocontrol agent of the present invention may be formulated in an acceptable carrier, for example, but not limited to a solid or liquid growth medium, preservation medium or the like. Acceptable carriers for spores may comprise, but are not limited to clay, alginate, diatomaceous earth or liquids containing suitable adjuvants, for example, but not limited to potato dextrose agar (PDA), gelatin, amino acids, sugars, surfactants and other solutes. Any carrier that permits the biocontrol agent to remain viable and pathogenic may be employed in the method of the present invention.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Isolation, Identification and Characterization of Bio-control Agent CL98–103

Diseased cleavers were collected in the districts of Vermilion, Vegreville, Lamont, Edmonton, and Peace River, Alberta, Canada. Diseased leaves, stems, flowers and seeds were air dried in a paper press, cut to appropriate size, and stored at 4° C. in envelopes. Tissue pieces with lesions were surface sterilized with 0.5% sodium hypochlorite solution and incubated on fresh potato dextrose agar (PDA; Difco, Detroit, Mich.). Fungi that grew from the lesions were isolated and Koch's postulates were performed for most samples shortly after each collection trip. Single conidial isolates of the recovered fungi were maintained in cryovials, each containing 2 ml of individual fungal isolate in 15% glycerol, and stored at −80° C. as stock cultures. From those collected plant materials, 138 fungal pathogens were isolated. A fungal isolate CL98–103 was selected after extensive screening on virulence to cleavers and safety to nine major crops (canola, wheat, barley, oats, flax, safflower, alfalfa, field pea, and lentil).

Inoculum Production

A cryovial of stock culture was warmed to room temperature in a water bath at 36° C., about 200 $\mu$l of suspension was aseptically placed on the surface of a potato dextrose agar (PDA) Petri plate and conidia were spread with a sterile glass rod. Petri plates were sealed and incubated at 22° C. with a 12 h photoperiod for 5–8 days. Single-conidium colonies were then made from the actively growing cultures and incubated under the same conditions. Conidia from the single-spore cultures were aseptically spread onto PDA and incubated as described above to increase inoculum. Conidia were harvested 15 days after incubation by flooding the plates with 10 ml of distilled water and scraping the surface of the colonies with a glass slide. The resulting suspensions were filtered through a layer of cheesecloth and conidial concentrations were determined with a hemacytometer.

Conidia were also produced in Richard's solution (RS; 50 g sucrose, 10 g $KNO_3$, 5 g $KH_2PO_4$, 2.4 g $MgSO_4$, 0.02 g $FeCl_3$, 1 L distilled water). A bulk of RS was prepared, pH was adjusted to 7.0 using 1N NaOH or HCl, and 200 ml aliquots were distributed into 500-ml Erlenmeyer flasks. Flasks containing the RS were then autoclaved for 15 min (100 kPa and 121° C.). After cooling, each flask was inoculated with 'seed' inoculum of *P. tabacinum* CL98–103. Inoculated flasks were incubated on an orbit shaker at about 150 rpm under ambient laboratory conditions (24±3° C.). After 3 d incubation, conidia were harvested by grinding the content of each flask using an electric hand blender (Braun Multipractic MR 20, Lunnfield, Mass., USA) and centrifuging 10 min to form a pellet (Sorvall RC-5B refrigerated superspeed centrifuge). The supernatant was decanted off and the conidial pellet was resuspended in an appropriate amount of 1% gelatin to achieve the desired inoculum concentration as determined with the aid of a haemocytometer.

Mycelial and spore characteristics of biocontrol agent CL98–103 were described through direct unaided inspection and microscopic observation. Both a light microscope (Nikon Inc., Melville, N.Y., USA) and scanning electron microscopy (SEM) (JEOL 6301F field emission SEM) were used. Colonies of CL98–103 grown on potato dextrose agar were moist, translucent white to pink in color, radially furrowed with concentric rings, and exhibited a felty appearance (aerial hyphae loosely aggregated into strands) (FIGS. 1A, 1B). CL98–103 is further characterized by simple or branched conidiophores and apical or lateral phialides that sometimes proliferate percurrently or have more than one conidiogenous locus with a cylindrical collarette and sinuous apex (FIG. 1C). Conidia are slightly asymmetric and thus appear slightly curved, hyaline, and 0 to 1 septate (FIGS. 1D, 1E). Germination can be bilateral or monolateral (FIGS. 1F, 1G, 1H).

The fungal isolate CL98–103 was identified as *Plectosporium tabacinum* (van Beyma) M. E. Palm, W. Gams et Nirenberg, an anamorph of *Plectoshphaerella cucumerina* (Lindf) W. Gams, at Centraalbureau voor Schimmelcultures, AG Baarn, The Netherlands. The strain was deposited in the ATCC as PTA-3463.

Example 2

Pathogenicity of *P. tabacinum* CL98–103

Effectiveness of P.Tabacinum CL98–103 to Control False Cleavers

Both Argentine canola and Polish canola with or without novel traits were selected for the pathogenicity test of *P. tabacinum* CL98–103. Three herbicide-tolerant cultivars, Invigor 2153 (Liberty Link), Quest (Roundup Ready), and 45A71 (Pursuit Smart), and two conventional cultivars Quantum and Inpulse, were selected as representatives of Argentine canola, while Hysin 111 and Reward were selected as representatives of Polish canola. For false cleavers, both herbicide-resistant and herbicide-susceptible biotypes were included in the pathogenicity test. False cleavers and canola cultivars were grown in greenhouse pots with 24/20±5° C. day/night temperature, a 16 h photoperiod, an average light intensity of 300 $\mu Em^{-2}s^{-1}$, and an average relative humidity of 45–50%. False cleavers seedlings at the one-whorl stage and canola seedlings at the one- or two-leaf stage were sprayed until run-off with $10^6$ to $10^7$ conidia per ml in 1% gelatin solution (Difco, Setroit, Mich., USA), using an H-set airbrush (Paasche Airbrush Company, Harwood Heights, Ill.) at a pressure of 100 kPa. Control plants were sprayed with 1% gelatin only. About 30 min after spraying, pots were placed in a dark dew chamber at 100% relative humidity at 22° C. for 24 h. Subsequently, pots were returned to the greenhouse for the remainder of the experiment. The disease reactions of herbicide-resistant and herbicide-susceptible false cleavers and canola to *P. tabacinum* CL98–103 were evaluated seven days after inoculation. On the basis of lesion type and size, plant response was rated at four levels: 0=lesions absent; 1=small, unexpanded lesions; 2=slightly to moderately expanded lesions; and 3=large lesions or dead plants. Dry weight was obtained by cutting aerial parts at soil level, drying in paper bags for 48 h at 70° C., and weighing.

Results showed that *P. tabacinum* CL98–103 caused large, necrotic lesions on leaves and stems of both herbicide-resistant and herbicide-susceptible false cleavers seedlings. The disease rating was 3 on both herbicide-resistant and herbicide-susceptible false cleavers (Table 1). *P. tabacinum* CL98–103, however, was not pathogenic to five cultivars of Argentine canola and two cultivars of Polish canola (Table 1). Without wishing to be bound by theory, the results suggest that canola is not a host of *P. tabacinum*, and that *P. tabacinum* CL98–103 may be safely used for the control of false cleavers in canola and other crops.

TABLE 1

Pathogenicity of *Plectosporium tabacinum* CL98-103 on herbicide-resistant and herbicide-susceptible false cleavers and various cultivars of canola*

| Plants | Host |
|---|---|
| *Galium spurium* (False cleavers) cleavers) | |
| Herbicide resistant type | 3 |
| Herbicide susceptible type | 3 |
| *Brassica napus* (Argentine Canola) | |
| cv. Invigor 2153 (Liberty Link) | 0 |
| cv. Quest (Roundup Ready) | 0 |
| cv. 45A71 (Pursuit Smart) | 0 |
| cv. Quantum (Conventional) | 0 |
| cv. Impulse (Conventional) | 0 |
| *Brassica rapa* (Canola) | |
| Hysin 111 | 0 |
| Reward | 0 |

*False cleavers seedlings at the 1-whorl stage and canola seedlings at the 1- to 2-leaf stage were inoculated with $10^6$ to $10^7$ spores/ml of *P. tabacinum* CL98-103, placed in a dew chamber at 22° C. for 24 h and subsequently maintained in a greenhouse.

**Host responses to *P. tabacinum* CL98-103 were rated seven days after inoculation with a 0 to 3 grading system: 0 = lesion absent; 1 = small, unexpanded lesions; 2 = slightly to moderately expanded lesions; and 3 = large lesions or dead plants.

The efficacy of *P. tabacinum* CL98–103 as a biocontrol agent towards false cleavers was determined under single or combined factors such as inoculum concentration, weed growth stage, dew period, temperature, and surfactant.

Effect of Conidial Concentration and Dew Period Duration on the Ability of *P. tabacinum* CL98–103 to Control False Cleavers The efficacy of *P. tabacinum* on both herbicide-resistant and herbicide-susceptible false cleavers was assessed under different conidial concentrations and dew period durations. Both herbicide-resistant and herbicide-susceptible false cleavers seedlings were produced in greenhouse pots, sprayed with a conidial concentration of $5\times10^6$, $1\times10^7$, $5\times10^7$, or $1\times10^8$ conidia per ml in 1% gelatin solution, placed in the dark dew chamber with 100% relative humidity at 22° C. for 8, 12, 16, or 20 h, and subsequently returned to the greenhouse. Seven days after spraying, mortality of plants and dry weight of aboveground biomass per pot were assessed. The *P. tabacinum* CL98–103 strain of this invention killed false cleavers seedlings when applied at a concentration of $10^7$ conidia per ml or greater with a 16–20 h dew period (FIG. 3). *P. tabacinum* CL98–103 therefore has potential for use as a bioherbicide for control of false cleavers. Another significant characteristic of *P. tabacinum* CL98–103 is its ability to kill herbicide-resistant false cleavers under the same conditions. The Efficacy of *P. tabacinum* CL98–103 to herbicide-resistant false cleavers seedlings was identical to herbicide-susceptible false cleavers seedlings in terms of plant mortality and percent dry weight reduction. Thus, the use of *P. tabacinum* CL98–103 may provide an option to manage herbicide-resistant false cleavers.

Effect of Conidial Concentration and Weed Growth Stage on Ability of *P. tabacinum* CL98–103 to Control False Cleavers The efficacy of *P. tabacinum* CL98–103 on false cleavers was assessed under different conidial concentrations and weed growth stages. Seedlings at the cotyledon, and 1-, 2-, 3-, 4-, or 5-whorl growth stage of false cleavers were inoculated with a conidial suspension at concentrations of $1\times10^8$, $1\times10^7$, $1\times10^6$, $1\times10^5$ or 0 conidia/ml. After inoculation, pots with inoculated seedlings were placed in a dark dew chamber for 24 h and then returned to the greenhouse. One hundred percent mortality of false cleavers seedlings was observed with the plant growth stage at the cotyledon- to 1-whorl stage and with an inoculum concentration of $10^7$ conidia/ml or greater (FIG. 4). The minimum inoculum concentration required to kill false cleavers seedlings was $1\times10^7$ conidia/ml. The 1-whorl growth stage or younger of false cleavers was the most susceptible. Increasing inoculum concentration increased weed control efficacy on older false cleavers seedlings.

Effect of Dew Period Duration on Ability of *P. tabacinum* CL98–103 to Control False Cleavers The efficacy of *P. tabacinum* CL98–103 on false cleavers was assessed under different dew period durations. False cleavers seedlings were produced in greenhouse pots, sprayed with a conidial concentration of $1\times10^7$spores per ml in 1% gelatin solution, placed in the dark dew chamber with 100% relative humidity at 22° C. for 0, 4, 8, 12, 16, 20, or 24 h. After the dew period treatment, pots were returned to the greenhouse. Seven days after spraying, mortality of plants and dry weight of aboveground biomass per pot were assessed. When adequate dew was provided, 100% mortality and dry weight reduction occurred (FIG. 5). The minimum dew period to achieve 100% mortality is 16 h without any formulation.

Effect of Dew Point Duration and Surfactant Concentration on Ability of *P. tabacinum* CL98–103 to Control False Cleavers The efficacy of *P. tabacinum* CL98–103 on false cleavers was assessed under different dew period durations and various concentrations of surfactant Silwet L-77. Since the minimum dew period to achieve 100% mortality is 16 h without any formulation, dew period may be a limiting factor for *P. tabacinum* CL98–103 to control false cleavers. Therefore, it is important to know whether a formulation with surfactant can reduce the dew period requirement for *P. tabacinum* CL98–103 to control false cleavers. False cleavers seedlings were produced in greenhouse pots, sprayed with a conidial concentration of $1\times10^7$ conidia per ml in 1% gelatin solution plus 0, 0.05%, or 0.1% Silwet L-77, placed in the dark dew chamber with 100% relative humidity at 22° C. for 0, 4, 8, 12, 16, 20, or 24 h. After the dew period treatment, pots were returned to the greenhouse. Seven days after spray, mortality of plants and dry weight of aboveground biomass per pot were assessed. Addition of 0.05–0.1% Silwet L-77 significantly reduced the minimum dew period for 100% mortality of false cleavers. An 8-h dew caused more than 70% mortality and over 80% dry weight reduction. When 12-h dew was provided, 100% mortality and dry weight reduction occurred. These results suggest that a formulation comprising the biocontrol agent of the present invention and Silwet L-77 may overcome the dew period limiting factor.

Effect of Dew Period Temperature and Duration on Mortality and Reduction in Dry Weight of False Cleavers Inoculated With *P. tabacinum* CL98–103

The efficacy of *P. tabacinum* CL98–103 on false cleavers was assessed under different dew period temperatures and durations. False cleavers seedlings at the 1-whorl stage were inoculated with conidial suspensions at a concentration of $1 \times 10^7$ conidia/ml. After inoculation, pots with inoculated seedlings were placed in the dew chamber at 100% humidity and temperatures of 15, 20, or 22° C. for 16 or 24 h and then returned to the greenhouse. Dew period temperature significantly affected the mortality and dry weight reduction of false cleavers seedlings caused by *P. tabacinum* CL98–103 (Table 2). When dew period temperature was 22° C., 100% mortality and dry weight reduction of false cleavers seedlings were observed with both 16 h and 24 h dew period durations. When dew period temperature was 20° C., a similar result was observed, but mortality and dry weight reduction of false cleavers seedlings with 24 h dew was greater than those with 16 h dew. When dew period temperature was 15 ° C., mortality and dry weight reduction of false cleavers seedlings were significantly less than those observed at dew period temperature of 20 or 22° C. A dew period temperature of 15° C. did not cause any mortality with 16 h dew, but resulted more than 86% mortality and dry weight reduction of false cleavers seedlings with 24 h of dew. An effective dew period temperature for disease development was above 15° C.

TABLE 2

Effect of dew period temperature and duration on mortality and reduction in dry weight of false cleavers inoculated with *Plectosporium tabacinum**

| | Dew period duration | | | |
|---|---|---|---|---|
| | 16 h | | 24 h | |
| Dew period temperature (° C.) | Mortality (%) ± SE** | Percent dry weight reduction (%) ± SE | Mortality (%) ± SE | Percent dry weight reduction (%) ± SE |
| 15 | 0 ± 0.0 a*** | 21.7 ± 3.5 b | 86.7 ± 5.7 b | 87 ± 7.4 b |
| 20 | 90.3 ± 6.3 a | 98 ± 4.5 a | 93 ± 8.7 a | 99 ± 1.3 a |
| 22 | 100 ± 0.0 a | 100 ± 0.0 a | 100 ± 0.0 a | 100 ± 0.0 a |

*False cleavers seedlings at 1-whorl stage were inoculated with conidial suspension at a concentration of $1 \times 10^7$ conidia/ml containing 1% gelatin (Difco Laboratories, Detroit, MI, USA) and 0.5–1% macerated PDA. Data represent means of four replicates.
**SE = Standard error
***Values in each column sharing the same letter are not significantly different according to Duncan's Multiple Range Test (DMRT) ($\propto \leqq 0.05$).

The Effect of Multiple, Repetitive Dew Periods on the Ability of *P. tabacinum* CL98–103 to Control False Cleavers The efficacy of *P. tabacinum* CL98–103 on false cleavers was assessed under multiple, repetitive dew periods. After inoculation, pots with inoculated seedlings were provided one of the following dark dew periods: (1) 0-h dew, (2) 8-h dew/16-h dry period on 1, 2, 3 or 4 consecutive days, (3) 12-h dew/12-h dry period on 1 or 2 consecutive days, (4) 16-h dew/8-h dry on 1 or 2 consecutive days; or (5) a single 24-h dew period. After treatment, pots were returned to the greenhouse. When provided with a continuous dew of 16-h or more, *P. tabacinum* CL98–103 caused 90–100% mortality and 92–100% dry weight reduction of false cleavers seedlings (Table 3). Repetitive 8-h dew on 1, 2, 3, or 4 consecutive days showed a general increase in dry weight reduction of cleavers. Two 12-h dew on consecutive days increased mortality of false cleavers seedlings, causing 83% mortality compared with 53% mortality with single 12-h dew. Similarly, two 12-h dew on consecutive days increased percent dry weight reduction (90%) as compared to single 12-h dew. The results suggest that disease development increases when inoculated seedlings are subjected to multiple, repetitive dew periods and that longer dew periods are more effective than shorter dew periods.

TABLE 3

Effect of repetitive dew periods on mortality and reduction in dry weight of false cleavers inoculated with *Plectosporium tabacinum* CL98-103*

| Dew period (h/day) | Mortality (%) | Dry weight reduction (%) |
|---|---|---|
| 0 | 0 c** | 10 c |
| 8 | 0 c | 15.6 c |
| 8;8 | 0 c | 28 bc |
| 8;8;8 | 0 c | 40.4 bc |
| 8;8;8;8 | 0 c | 45 b |
| 12 | 53 b | 77.4 a |
| 12;12 | 83 a | 90.1 a |
| 16 | 90 a | 92.4 a |
| 24 | 100 a | 100 a |

*Seedlings of false cleavers at the 1-whorl growth stage were inoculated with a conidial suspension at a concentration of $1 \times 10^7$ conidia/ml containing 1% gelatin (Difco Laboratories, Detroit, MI, USA) and 0.5–1% macerated PDA. Data represent means of four replicates.
**Values in each column having the same letter are not significantly different according to DMRT at the 5% significance level.

Host Range of *P. tabacinum* CL98–103.

Using the modified centrifugal phylogenetic and varietal strategy (Wapshere, 1974), 35 plant species in 26 genera and 12 families were selected for the host range trial (Table 4). Test plants were grown from seed or propagated vegetatively depending on the species being tested and availability of material. For each species, two sets of test plants (each set containing 15 plants) were prepared. One set was inoculated with *P. tabacinum* CL98–103 and the other set served as uninoculated controls. For the inoculated treatment, seedlings of selected plant species at the 2- to 3-leaf stage were sprayed to run-off with $1 \times 10^7$ conidia per ml in 1% gelatin solution. For uninoculated control, seedlings of selected plant species at the 2- to 3-leaf stage were sprayed with 1% gelatin. About 30 min after spraying, pots were placed in the dark dew chamber with 100% relative humidity at 22° C. for 24 h. Subsequently, pots were returned to the greenhouse for the remainder of the experiment. Disease severity was visually assessed daily until the $14^{th}$ day after inoculation by using the 0–11 rating scale by Horsfall and Barrett(1945).

All seedlings of false cleavers serving as positive controls were killed when subjected to a 24 h dew period. Cleavers (*Galium aparine* L.), another weed species in the Galium weed complex in western Canada, was also killed with 24 h dew. The findings in this study demonstrate that *P. tabacinum* CL98–103 may be used for the control of two weedy Galium species. Results also showed that other species in the genus Galium are immune to *P. tabacinum*. Hosts of *P. tabacinum* CL98–103 in the Rubiaceae family were restricted to the Section Kolgyda (false cleavers and cleavers) in the Genus Galium, the tribe Rubieae, and the subfamily Rubiodieae. The use of this strain of *P. tabacinum* should therefore be safe to non-weedy native Galium species and other plant species in this family.

*P. tabacinum* CL98–103 caused slight symptoms with limited expansion of lesions on sunflower (*Helianthus annuus* L.) with the 24 h dew period treatment. Lesion expansion covered less than 10% of inoculated leaves 2 weeks after inoculation and no stem lesions were observed. Lesions did not spread to emerging uninoculated leaves. Similarly, *P. tabacinum* CL98–103 caused small (<0.5 mm) brown flecks on inoculated leaves of flax (*Linum usitatissimum* L.), safflower (*Carthamus tinctorius* L.), melon (*Cucumis melo* L.), zucchini (*Cucubita pepo* L.), and tomato (*Lycopersicon esculentum* Mill.) with a 24 h dew period treatment. However, these small flecks did not expand during the 2-week observation period and lesions covered less than 3% of infected leaves.

All other plant species tested were immune to *P. tabacinum* CL98–103. Further, *P. tabacinum* has never been reported to cause crop diseases in Canada. The detection of natural infection of*P. tabacinum* CL98–103 on cleavers but not on any crops in western Canada suggests that this fungus can be used as a bioherbicide to control cleavers.

TABLE 4

Test plant species used for host-specificity screening of *Plectosporium tabacinum* CL98-103 against false cleavers (*Galium spurium*) based on the modified centrifugal phylogenetic and varietal strategy

| | |
|---|---|
| Rubiaceae | 1. *Galium spurium* L. (False cleavers) |
| | 2. *G. aparine* L. (Cleavers) |
| | 3. *G. boreale* L. (Northern bedstraw) |
| | 4. *G. triflorum* Michx. (Fragrant bedstraw) |
| | 5. *G. trifidum* L. (Three petal bedstraw) |
| | 6. *G. mollugo* L. (Common hedge bedstraw) |
| | 7. *G. trifidum* L. (Three petal bedstraw) |
| | 8. *Asperula arvensis* L. (Blue woodruff) |
| | 9. *Sherardia arvensis* L. (Blue field madder) |
| | 10. *Houstonia longifolia* L. (Longleaf summer blue) |
| | 11. *Cephalanthus occidentalis* L. (Button bush) |
| Brassicaceae | 12. *Brassica napus* L. (Argentine Canola) |
| | cv. Invigor 2153 (Liberty Link) |
| | cv. Quest (Roundup Ready) |
| | cv. 45A71 (Pursuit Smart) |
| | cv. Quantum (Conventional) |
| | cv. Impulse (Conventional) |
| | 13. *Brassica rapa* L. (Polish Canola) |
| | cv. Hysyn 111 |
| | cv. Reward |
| | 14. *Brassica oleracea* L. var. botrytis L. (Cauliflower, cv. Snowball A) |
| Poaceae | 15. *Triticum aestivum* L. (Wheat, cv. Katepwa) |
| | 16. *Hordeum vulgare* L. (Barley, cv. Bridge) |
| | 17. *Avena sativa* L. (Oats, cv. Unknown) |
| Fabaceae | 18. *Pisum sativum* L. (Pea, cv. Radley) |
| | 19. *Medicago sativa* L. (Alfalfa, cv. Algonquin) |
| | 20. *Lens culinaris* Medic. (Lentil, cv. Laird) |
| Linaceae | 21. *Linum usitatissimum* L. (Flax, cv. Norlin) |
| Asteraceae | 22. *Helianthus annuus* L. (Sunflower cv. S6140) |
| | 23. *Carthamus tinctorius* L. (Safflower cv. unknown) |
| | 24. *Taraxium officinale* Weber in Wiggers (Dandelion) |
| Solanaceae | 25. *Solanum tuberosum* L. (Potato cv. Normondy cv. Russet burbank) |
| | 26. *Lycopersicon esculentum* L. (Tomato cv. Bush Beef Steak) |
| | 27. *Nicotiana tabacum* L. (Tobacco cv. Turkish) |
| Balsaminaceae | 28. *Impatiens balsami* L. (Balsam) |
| Apiaceae | 29. *Apium graveolens* L. (Celery cv. Utah Tall Green) |
| | 30. *Pastinaca sativa* (Parsnip cv. All American) |
| Violaceae | 31. *Viola odorata* (English violet) |
| Cucurbitaceae | 32. *Cucumis melo* L. (Melon cv. Hales Best) |
| | 33. *Cucurbita pepo* L. (Zucchini cv. Summer Squash) |
| | 34. *Cucurbita pepo* L. (Pumpkin cv. Big Mac) |
| Asclepiadaceae | 35. Asclepias sp. (Milkweed) |

Example 3

Establishment of Culture Conditions for Enhanced Growth and Spore Production of *P. tabacinum* CL98103

Culture conditions were varied to examine the growth, spore germination, and sporulation requirements of *P. tabacinum* CL98–103 on standard agar media. Fourteen different standard agar media over a range of light regimes, pH, and temperatures were tested. Culture media tested were water agar (WA), Potato dextrose agar (PDA), Cooke rose bengal agar (CRBA), dextrose tryptone agar (DTA), Czapek Dox agar (CDA), tryptic soy agar (TSA), malt extract agar (MEA), sabouroud dextrose agar (SDA), oatmeal agar (OMA), prune agar (PA), lima bean agar (LBA), cornmeal agar (CA), V-8 juice agar (VA), and synthetic nutrient poor agar (SNA). Results demonstrated that PDA is a good medium for growth and sporulation of *P. tabacinum* CL98–103 (Table 5). On standard agar media, growth and sporulation of *P. tabacinum* was not appreciably influenced by light regime. An effective temperature for mycelial growth was between about 22 and about 25° C., but an effective temperature for sporulation was either about 20 or about 30° C., depending upon the nutrient medium (FIG. 7). It appeared that between 15 and 20° C. changes in the spore germination capabilities of this isolate occurred as over 90% of spores germinated when temperatures were about 20° C. or above, while less than 10% of spores germinated when temperatures were about 15° C. or below.

TABLE 5

Effect of culture medium and light regime on mycelial growth and sporulation of *Plectosporium tabacinum* CL98-103*

| | Colony diameter (mm) | | Number of spores/plate ($\times 10^8$) | |
|---|---|---|---|---|
| Medium | Light | Dark | Light | Dark |
| Potato dextrose agar | 63.3 cde** | 54.2 d | 6.942 a | 6.458 a |
| V-8 juice agar | 76 a | 71.8 a | 2.113 b | 1.653 b |
| Czapek-Dox agar | 66.3 cd | 67.5 b | 1.046 c | 0.933 b |
| Oatmeal agar | 62.7 c | 61.8 c | 0.818 c | 0.941 b |
| Lima bean agar | 72.3 b | 69.8 ab | 0.588 cd | 0.535 b |
| Tryptic soy agar | 54.8 f | 57.4 d | 0.561 cd | 0.208 b |
| Dextrose Tryptone agar | 54.2 f | 55.7 d | 0.099 d | 0.159 b |
| Cooke rose bengal agar | 22.8 h | 40.2 e | 0.028 d | 0.092 b |
| Prune agar | 67.7 c | 63.5 c | 0.021 d | 0.014 b |
| Malt extract agar | 57.3 f | 56.2 d | 0.008 d | 0.008 b |
| Synthetic nutrient-poor agar | 74.3 ab | 72.8 a | 0.006 d | 0.007 b |
| Sabouraud dextrose agar | 38.8 g | 39 e | 0.006 d | 0.006 b |
| Water agar | 64.5 cde | 62.7 c | 0.005 d | 0.003 b |
| Cornmeal agar | 72.7 b | 72.7 a | 0.004 d | 0.006 b |

*Mycelial growth was measured after 14 days of incubation. The number of spores/plate was determined after 21 days of incubation.
**Values in each column sharing the same letter are not significantly different according to DMRT ($\propto \leqq 0.05$).

Submerged liquid culture spore production is the preferred technique for mass production of biocontrol agents because the technology is readily available and the scale-up process from the research phase to the development phase is relatively easy. Conditions required for submerged liquid culture spore production and resulting weed control efficacy of *P. tabacinum* CL98–103 was assessed, including the effect of liquid culture medium and pH and the effect of carbon-nitrogen composition such as carbon source, nitrogen source, carbon concentration, and carbon-to-nitrogen ratio.

Liquid culture media tested included: Tryptic Soy broth (TSB), Czapek-Dox broth (CDB), Yeast Extract broth (YEB), Nutrient Broth (NB), Potato Dextrose broth (PDB), Malt Extract broth (MEB), Richard's solution (RS), modified Richard's solution (MRS) (Daniel et al. 1973), Colletotrichum truncatum medium (CTM) (Jackson 1997), V-8 juice medium (VM), and Trichoderma medium (TM) (Tabachnik 1989). The pH of culture media was not adjusted. Results indicate that a variety of liquid culture media may be employed for spore production of *P. tabacinum* CL98–103 (Table 6).

TABLE 6

Effect of liquid culture medium on spore production and efficacy against false cleavers of *Plectosporium tabacinum* CL98-103*.

| Medium | Spore production ($10^7$ spores/ml) | Efficacy** (%) |
|---|---|---|
| V-8 juice medium (VM) | 2.62 a | 84 ab |
| Modified Richard's solution (MRS) | 2.22 a | 60.5 c |
| Yeast extract broth (YEB) | 1.43 b | 79.4 bc |
| Richard's solution (RS) | 1.06 c | 97.1 ab |
| Czapek-Dox broth (CDB) | 0.49 d | 62.1 c |
| Trichoderma medium (TM) | 0.31 de | 100 a |
| Tryptic soy broth (TSB) | 0.3 de | ND*** |
| Potato dextrose broth (PDB) | 0.16 e | ND |
| Nutrient broth (NB) | 0.05 e | ND |
| *Colletotrichum truncatum* medium (CTM) | 0.04 e | ND |
| Malt extract broth (MEB) | 0.02 e | ND |

*The spores were harvested after 72 h incubation.
**Weed control efficacy was based on the dry weight data (DW) and calculated as follows: weed control efficacy (%) = (DW in uninoculated control − DW in inoculated treatment)/DW in uninoculated control * 100.
***ND denotes no test was done.
****Values in each column sharing the same letter are not significantly different according to DMRT ($\alpha \leqq 0.05$).

Liquid culture medium pH also profoundly affected submerged liquid culture spore production of *P. tabacinum* CL98–103 (FIG. 7). For example, when the pH of RS remained unadjusted at 3.9 as in the liquid culture medium study, only $1.06\times10^7$ spores/ml were produced (Table 6), while spore production in RS adjusted to pH 7 prior to inoculation was about seven times higher ($7.7\times10^7$ spores/ml; FIG. 7). An effective pH for spore production of *P. tabacinum* CL98–103 is 7 for RS medium.

Liquid culture medium carbon-nitrogen composition such as carbon source, nitrogen source, carbon concentration, and carbon-to-nitrogen ratio was also varied to evaluate their effects on spore production, spore characteristics, and weed control efficacy of *P. tabacinum* CL98–103. Fourteen different nitrogen sources were tested including corn gluten meal (12.42 g $L^{-1}$), corn steep liquor (23.99 g $L^{-1}$), malt extract (25 g $L^{-1}$), casein (10.1 g $L^{-1}$), yeast extract (13.24 g $L^{-1}$), bovine serum albumin (9.06 g $L^{-1}$), cottonseed oil (77.12 g $L^{-1}$), casamino acids (14.04 g $L^{-1}$), sodium nitrate (8.51 g $L^{-1}$), aspargine (6.62 g $L^{-1}$), glutamic acid (14.74 g $L^{-1}$), urea (3 g $L^{-1}$), ammonium sulfate (6.62 g $L^{-1}$), and potassium nitrate (10 g $L^{-1}$). Ten different carbon sources were tested including glucose, fructose, galactose, glycerol, potassium acetate, acetic acid, cellulose, corn starch, citrate, and sucrose. Eight carbon concentrations of the medium (i.e. sucrose) were tested including 4.2, 8.4, 12.6, 16.8, 21.0, 25.2, 29.4, or 33.6 g/L. Six C:N ratios, i.e. 40:1, 20:1, 15:1, 10:1, 7.5:1, and 5:1, were evaluated under three different levels of carbon concentration, i.e. 8.4, 21.0, and 33.6 g $L^{-1}$. Results demonstrated that the carbon-nitrogen composition of the medium including nitrogen source, carbon source, carbon concentrations, and C:N ratios influences spore production, spore size, spore nuclear number, and/or weed control efficacy of *P. tabacinum* CL98–103. It has also been found that the carbon-nitrogen composition of the medium that allowed the production of the highest number of spores did not result in the production of spores with the highest efficacy against false cleavers when spores were applied to plants at the same concentration and under the same experimental conditions. For production of a high number of *P. tabacinum* CL98–103 spores with good weed control efficacy, a good nitrogen source and carbon source may be potassium nitrate (Table 7) and sucrose or cornstarch (Table 8), respectively. Sucrose as the carbon source produced moderate spore numbers ($2.45\times10^7$ spores/ml), but spores produced in this carbon source caused 99.8% dry weight reduction of false cleavers. Spore production using corn starch ($3.68\times10^7$ spores/ml) was close to the highest spore numbers, but spores produced with corn starch caused a percent dry weight reduction of false cleavers (94.6%) similar to that of sucrose (99.8%). Since corn starch is an agricultural-based product and readily available at a low cost, it may be a good carbon source for mass production of this potential bioherbicide.

A medium comprising a high carbon concentration and a low carbon concentration inhibited spore production of *P. tabacinum* CL98–103 (Table 9). A carbon concentration of 12.6 g/L produced high spore numbers and spores produced at this carbon concentration caused the significant dry weight reduction of false cleavers. The C:N ratio affected spore production but not weed control efficacy. A C:N ratio of 7.5:1 is effective for spore production of *P. tabacinum* CL98–103 (FIG. 8). Based on the results, an effective liquid medium for production of a high number of *P. tabacinum* CL98–103 spores with good weed control efficacy may be constructed using a C:N ratio of 7.5:1 with 12.6 g/L sucrose or corn starch, and 10 g/L potassium nitrate.

TABLE 7

Effect of nitrogen source on spore production, spore nuclear number, spore size, and efficacy against false cleavers of *Plectosporium tabacinum* CL98-103 in a basal salts medium based on Richard's solution*

| Nitrogen sources | Spore production ($10^7$ spores/ml) | Nuclear number | Spore length ($\mu$m) | Spore width ($\mu$m) | Efficacy** (%) |
|---|---|---|---|---|---|
| potassium nitrate (control) | 2.45 bc | 1.8 a | 7.4 a | 3.4 a | 100 a |
| corn gluten meal | 6.63 a | 1.6 a | 7.4 a | 3.2 a | 80.8 ab |
| corn steep liquor | 2.7 b | 1.7a | 7.1 a | 3 a | 91.7 a |
| glutamic acid | 1.72 bcd | 1.9 a | 7.4 a | 3.3 a | 52.9 c |
| asparagines | 1.67 bcd | 1.6 a | 7 a | 3 a | 50.7 c |
| casamino acids | 1.54 bcd | 1.8 a | 7.6 a | 3.1 a | 93.5 a |
| yeast extract | 1.54 bcd | 1.8 a | 7.5 a | 3.4 a | 100 a |
| sodium nitrate | 1.48 bcd | 1.9 a | 7.3 a | 3.2 a | 65.6 bc |
| casein | 0.83 bcd | ND*** | ND | ND | ND |
| urea | 0.66 bcd | ND | ND | ND | ND |
| malt extract | 0.2 cd | ND | ND | ND | ND |
| ammonium sulfate | 0.1 3 cd | ND | ND | ND | ND |
| bovine serum albumin | 0.12 cd | ND | ND | ND | ND |
| cottonseed oil | 0 d | ND | ND | ND | ND |

*For all nitrogen source treatments, a carbon concentration of 21 g/L and a C:N ratio of 15:1 were maintained in the basal salt medium. The spores were harvested after 72 h incubation.
**Weed control efficacy was based on the dry weight data (DW) and calculated as follows: weed control efficacy (%) = (DW in uninoculated control − DW in inoculated treatment)/DW in uninoculated control * 100.
***ND denotes no test was done.
****Values in each column sharing the same letter are not significantly different according to DMRT ($\alpha \leqq 0.05$).

TABLE 8

Effect of carbon source on spore production, spore nuclear number, spore size, and efficacy against false cleavers of *Plectosporium tabacinum* CL98-103 in a basal salts medium based on Richard's solution*

| Carbon sources | Spore production ($10^7$ spores/ml) | Nuclear number | Spore length (μm) | Spore width (μm) | Efficacy** (%) |
|---|---|---|---|---|---|
| Sucrose (control) | 2.45 b**** | 1.9 a | 8.3 a | 3.9 b | 99.8 a |
| galactose | 3.81 a | 1.7 a | 7.6 a | 4.4 a | 62.4 b |
| corn starch | 3.68 a | 1.8 a | 6.3 b | 3.4 c | 94.6 a |
| cellulose | 1.62b c | 1.5 a | 6.9 b | 3 d | 46 c |
| glucose | 0.09 cd | 1.4 a | 6.9 b | 3.9 b | 63.5 b |
| fructose | 0.08 cd | 1.4 a | 7.3 ab | 3.9 b | 96 a |
| citric acid | 0.06 cd | 1.7 a | 8.I a | 3.7 b | 98.9 a |
| glycerol | 0.004 d | ND*** | ND | ND | ND |
| potassium acetate | 0.002 d | ND | ND | ND | ND |
| acetic acid | 0 d | ND | ND | ND | ND |

*For all carbon source treatments, a carbon concentration of 21 g/L and a C:N ratio of 15:1 were maintained in the basal salt medium. The spores were harvested after 72 h incubation.
**Weed control efficacy was based on the dry weight data (DW) and calculated as follows: weed control efficacy (%) = (DW in uninoculated control − DW in inoculated treatment)/DW in uninoculated control * 100.
***ND denotes no test was done.
****Values in each column sharing the same letter are not significantly different according to DMRT (∝ ≦ 0.05).

TABLE 9

Effect of carbon concentration on spore production, spore nuclear number, spore size, and efficacy against false cleavers of *Plectosporium tabacinum* in a basal salts medium based on Richard's solution*

| Carbon concentration (g/L) | Spore production ($10^7$ spores/ml) | Nuclear number | Spore length (μm) | Spore width (μm) | Efficacy** (%) |
|---|---|---|---|---|---|
| 4.2 | 5.23 bcd*** | 1.6 a | 7.2 a | 3 a | 58.8 b |
| 8.4 | 6.25 ab | 1.7 a | 7.6 a | 3.2 a | 81.9 a |
| 12.6 | 6.77 a | 1.7 a | 7.5 a | 3.1 a | 90.0 a |
| 16.8 | 5.68 abc | 1.9 a | 7.6 a | 3.2 a | 88.3 a |
| 21 | 5.08 bcd | 1.7 a | 7.2 a | 3.3 a | 83.5 a |
| 25.2 | 4.65 cde | 1.7 a | 7.4 a | 3 a | 90.8 a |
| 29.4 | 4.37 de | 1.7 a | 7 a | 3.3 a | 83.4 a |
| 33.6 | 3.68 e | 1.8 a | 7 a | 3.1 a | 81.9 a |

*While maintaining a C:N ratio of 15:1, the carbon concentration of the basal salt medium (Richard's solution) was adjusted to 4.2, 8.4, 12.6, 16.8, 21.0, 25.2, 29.4, or 33.6 g/L by adding variable amount of sucrose and potassium nitrate. The spores was harvested and counted after 72 h incubation on a rotary shaker at 150 rpm.
**Weed control efficacy was based on the dry weight data (DW) and calculated as follows: weed control efficacy (%) = (DW in uninoculated control − DW in inoculated treatment)/DW in uninoculated control * 100.
***Values in each column sharing the same letter are not significantly different according to DMRT (∝ ≦ 0.05).

All Citations are Herein Incorporated by Reference.

The present invention has been described with regard to preferred embodiments. However, it will be obvious to persons skilled in the art that a number of variations and modifications can be made without departing from the scope of the invention as described herein.

References

Each of the below references are hereby incorporated by reference for any purpose.

Chung, Y. R., S. J. Koo, H. T. Kim, and K. Y. Cho. 1998. Potential of an indigenous fungus, *Plectosporium tabacinum*, as a mycoherbicide for control of arrowhead (*Sagittaria trifolia*). Plant Dis. 82: 657–660.

Hall, L. M, K. M. Stromme, G. P. Horsman, and M. D. Devine. 1998. Resistance to acetolactate synthase inhibitors and quinclorac in a biotype of false cleavers (*Galium spurium*). Weed Sci. 46:390–396.

Horsfall, J. G. and R. W. Barrett .1945. An improved grading system for measuring plant diseases. Phytopathol. 35:655.

Malik, N. and W. H. Vanden Born. 1987. Growth and development of false cleavers (*Galium spurium* L.). Weed Sci. 35:490–495.

Malik, N. and W. H. Vanden Born. 1988. The biology of Canadian weeds. 86. *Galium aparine* L. and *Galium spurium* L. Can. J. Plant Sci. 68: 481–499.

Smither-Kopperl, M. L., R. Charudattan, and R. D. Berger. 1999. *Plectosporium tabacinum*, a pathogen of the invasive aquatic weed *Hydrilla verticillata* in Florida. Plant Dis. 83: 24–28.

Thomas, A. G., B. Frick, and L. M. Hall. 1998. Weed population shifts in Alberta. Agriculture and Agri-Food Canada, Saskatoon, pp. 1.

We claim:

1. A biocontrol agent comprising isolated *Plectosporium tabacinum* CL98–103 deposit number PTA-3463 (ATCC).

2. A composition comprising the biocontrol agent of claim 1 and a carrier.

3. The composition of claim 2, wherein said carrier comprises clay, alginate, diatomaceous earth, growth medium, or a combination thereof.

4. The composition of claim 3, wherein said growth medium is selected from the group consisting of solid growth medium and liquid growth medium.

5. The composition of claim 4, wherein said growth medium is solid growth medium.

6. The composition of claim 5 wherein said solid growth medium is selected from the group consisting of potato dextrose agar, Czapek-Dox agar, lima bean agar, V-8 juice agar, oatmeal agar, tryptic soy agar, dextrose tryptone agar, Cooke rose bengal agar, prune agar, malt extract agar, synthetic nutrient poor agar, Sabouraud dextrose agar, water agar and cornmeal agar.

7. The composition of claim 4, wherein said growth medium is liquid growth medium.

8. The composition of claim 7, wherein said liquid growth medium is selected from the group consisting of V-8 juice medium, Modified Richard's solution (MRS), Yeast extract broth (YEB), Richard's solution (RS), Czapek-Dox broth (CDB), Trichoderma medium (TM), Tryptic soy broth (TSB), Potato dextrose broth (PDB), Nutrient broth (NB), *Colletotrichum truncatum* medium (CTM), Malt extract broth (MEB) and a combination thereof.

9. A method for the biocontrol of weeds comprising, administering an effective amount of the biocontrol agent of claim 1 to said weeds under non-aquatic conditions.

10. A method for the biocontrol of weeds comprising, administering to said weeds an effective amount of the biocontrol agent of claim 1.

11. The method of claim 10, wherein said biocontrol agent is administered to said weed at about the one whorl stage or earlier.

12. The method of claim 10, wherein said weeds are cleavers.

13. The method of claim 12, wherein said cleavers comprise herbicide-resistant cleavers, herbicide-susceptible cleavers, or a combination thereof.

14. The method of claim 12, wherein said biocontrol agent is administered to said cleavers in conjunction with an herbicide.

15. The method of claim 10, wherein said biocontrol agent further comprises a surfactant.

16. The method of claim 15, wherein said surfactant is Silwet L-77.

17. The method of claim 16, wherein said surfactant is present in an amount of about 0.05% to about 0.1% by volume.

18. A composition comprising spores of *Plectosporium tabacinum* CL98–103 deposit number PTA-3463 (ATCC) and a carrier.

19. A method for the biocontrol of weeds comprising, administering to said weeds an effective amount of the composition of claim 18.

20. A method for the biocontrol of weeds comprising, administering an effective amount of the composition of claim 18 to said weeds under non-aquatic conditions.

* * * * *

UNITED STATES PATENT AND TRADEMARK OFFICE

CERTIFICATE OF CORRECTION

PATENT NO. : 6,686,316 B2
DATED : February 3, 2004
INVENTOR(S) : Zhang et al.

It is certified that error appears in the above-identified patent and that said Letters Patent is hereby corrected as shown below:

Column 1,
Line 6, delete "Application No. 2,324,215" and insert -- Application No. 2,325,215 --, therefor.

Signed and Sealed this

Twenty-seventh Day of July, 2004

JON W. DUDAS
*Acting Director of the United States Patent and Trademark Office*